(12) United States Patent
Staib et al.

(10) Patent No.: US 7,188,034 B2
(45) Date of Patent: Mar. 6, 2007

(54) METHOD AND DEVICE FOR MONITORING AN ANALYTE CONCENTRATION IN THE LIVING BODY OF A HUMAN OR ANIMAL

(75) Inventors: Arnulf Staib, Oftersheim (DE); Rainer Hegger, Obcrursel (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 11/113,606

(22) Filed: Apr. 25, 2005

(65) Prior Publication Data
US 2005/0240356 A1 Oct. 27, 2005

(30) Foreign Application Priority Data
Apr. 24, 2004 (DE) .................. 10 2004 020 160

(51) Int. Cl.
*G01N 31/00* (2006.01)
(52) U.S. Cl. ........................... 702/22; 600/345
(58) Field of Classification Search ............ 702/22, 702/19, 25, 117; 600/345, 310; 706/44; 436/518, 95; 250/573, 287; 435/14
See application file for complete search history.

(56) References Cited

U.S. PATENT DOCUMENTS

| 5,482,035 A | 1/1996 | Paloheimo |
| 5,507,288 A | 4/1996 | Bocker et al. |
| 5,748,851 A | 5/1998 | Iokibe et al. |
| 5,971,922 A | 10/1999 | Arita et al. |
| 6,272,480 B1 * | 8/2001 | Tresp et al. .................... 706/44 |
| 6,546,269 B1 * | 4/2003 | Kurnik ....................... 600/345 |
| 2002/0106709 A1 | 8/2002 | Potts et al. |

FOREIGN PATENT DOCUMENTS

| DE | 10343863.7 | | 4/2005 |
| EP | 1102194 A2 * | | 5/2001 |
| EP | 1 518 495 A1 | | 3/2005 |

OTHER PUBLICATIONS

Schreiber, T., "Interdisciplinary application of nonlinear time series methods", Physics Reports 308, pp. 1-64, (1999).
Kennel, M.B. et al., "Determining embedding dimension for phase-space reconstruction using a geometrical construction", Phys. Rev. A 45, p. 3403, (1995).
Otto, M., "Chemometrics—Statistics and Computer Application in Analytical Chemistry", Wiley-VCH, Weinheim (Germany), pp. 124-133, (1999).

(Continued)

*Primary Examiner*—Bryan Bui
*Assistant Examiner*—Xiuqin Sun
(74) *Attorney, Agent, or Firm*—Barnes & Thornburg LLP (57) ABSTRACT

The present invention generally relates to a method and a device for monitoring an analyte concentration in the living body of a human or animal. In particular to a method and device for determining analyte values $y(t_n)$ correlating with the concentration to be determined are determined for consecutive points in time $t_n$. The analyte values $y(t_n)$ is used to predict a prediction value for an analyte $y(t_{n_0}+\Delta t)$ over a prediction period $\Delta t$.

15 Claims, 4 Drawing Sheets

OTHER PUBLICATIONS

Press, W.H., et al., "Numerical Recipes—The Art of Scientific Computing", Cambridge University Press, Cambridge (UK), pp. 52-61, (1989).

Iokibe, T., "Deterministic nonlinear short-term predication", Handbook of Fuzzy Computation, pp. G.16.4:1-G.16,4:11, (1998).

Smith, A.F.M., et al., "Monitoring Kidney Transplant Patients", The Statistician 32, pp. 46-54, (1983).

Gordon, K., et al., "Modeling and Monitoring Biomedical Time Series", Journal of the American Statistical Association 85, pp. 328-337, (1990).

Gordon, K., et al., "The multi-state Kalman Filter in medical monitoring", Computer Methods and Programs in Biomedicine 23, pp. 147-154, (1986).

* cited by examiner

METHOD AND DEVICE FOR MONITORING AN ANALYTE CONCENTRATION IN THE LIVING BODY OF A HUMAN OR ANIMAL

REFERENCE TO RELATED APPLICATIONS

The present application claims priority to German Patent Application No. 10 2004 020 160.9, filed Apr. 24, 2004, which is hereby incorporated by reference in its entirety.

TECHNICAL FIELD

The present invention generally relates to a method and a device for monitoring an analyte concentration in the living body of a human or animal. In particular to a method and device for determining analyte values $y(t_n)$ and using the analyte value in predicting a value for the analyte over a period of time.

BACKGROUND

Study results have demonstrated that extremely serious long-term corollaries of diabetes mellitus (for example blinding of the patient due to retinopathy) can be prevented by continuous in vivo monitoring of the time profile of the glucose concentration. This allows the dosage of the medication required (insulin) to be adjusted exactly at any point in time and thus the blood sugar levels to be kept within narrow limits at all times like in a healthy person. A method of this type and a suitable device are described in U.S. Pat. No. 5,507,288, for example. The patent describes in particular the continuous monitoring of the glucose concentration in the body of a patient, which is of crucial medical significance.

In order for the medication process to be as efficient as possible it is desired to be able to determine not only a current value of the concentration of an analyte, but also predict future concentration values. The prediction of future values of the concentration of an analyte is of particular significance in the case of diabetes, not only to counteract an increase of the blood glucose concentration beyond a critical value by administering insulin, but also to alert the patient to a decrease of the blood glucose concentration.

The prediction of a future concentration of an analyte value in the living body of a human or animal is made significantly more complicated by the fact that concentration values depend not only on historic values, but also on other parameters, such as food and medication intake or physical exercise.

A method for monitoring the blood glucose concentration is known from U.S. Pat. No. 6,272,480 B1, in which an artificial neuronal network is used to derive a prediction of future blood glucose values from a time series of glucose concentrations that were measured. However, a significant disadvantage of artificial neuronal networks is that they need to be trained prior to their use and yield unreliable results when confronted with time series data outside of their training range.

From EP 1102194 A2, a method is known in which blood glucose concentration values measured at consecutive points in time are extrapolated taking into consideration patient-specific data, such as, in particular, any carbohydrate intake and insulin administration. For practical applications, the need to account for such patient-specific data is a major disadvantage, since accounting for such data is difficult and often error-prone.

SUMMARY

It is against the above background that the present invention proves certain unobvious advantages and advancements over the prior art.

The present invention provides means for continuous monitoring of the concentration of an analyte in the living body of a human or animal and predicting future concentration values. In particular, in this method aside from data of historic concentration values, would not require any patient-specific data, such as food or insulin intake, for the prediction of future concentration values.

A method for continuous monitoring of an analyte concentration by determining its progression in the living body of a human or animal, in which analyte values $y(t_n)$ correlating with the concentration to be determined are determined for consecutive points in time $t_n$. The analyte values are then used for predicting a prediction value for an analyte value $y(t_{n_0}+\Delta t)$ over a prediction period $\Delta t$.

The method according to the invention can be applied in several steps in order to determine from a prediction value $y(t_{n_0}+\Delta t)$ another prediction value $y(t_0+2\Delta t)$ even further in the future. A prediction value $y(t_0+n\Delta t)$ can thus be determined by multiple application of the method.

These and other features and advantages of the present invention will be more fully understood from the following detailed description of the invention taken together with the accompanying claims. It is noted that the scope of the claims is definitely by the recitations therein and not by the specific discussion of the features and advantages set forth in the present description.

BRIEF DESCRIPTION OF THE DRAWINGS

The invention and preferred embodiments are illustrated in more detail in the following with reference to the figures. The features illustrated and described in the following can be used individually or in combination in order to create preferred further refinements of the invention. In the figures.

Skilled artisans appreciate that elements in the figures are illustrated for simplicity and clarity and have not necessarily been drawn to scale. For example, the dimensions of some of the elements in the figure may be exaggerated relative to other elements to help improve understanding of the embodiment(s) of the present invention.

DETAILED DESCRIPTION

The following description of the preferred embodiment is merely exemplary in nature and is in no way intended to limit the invention or its application or uses.

Figure 1:
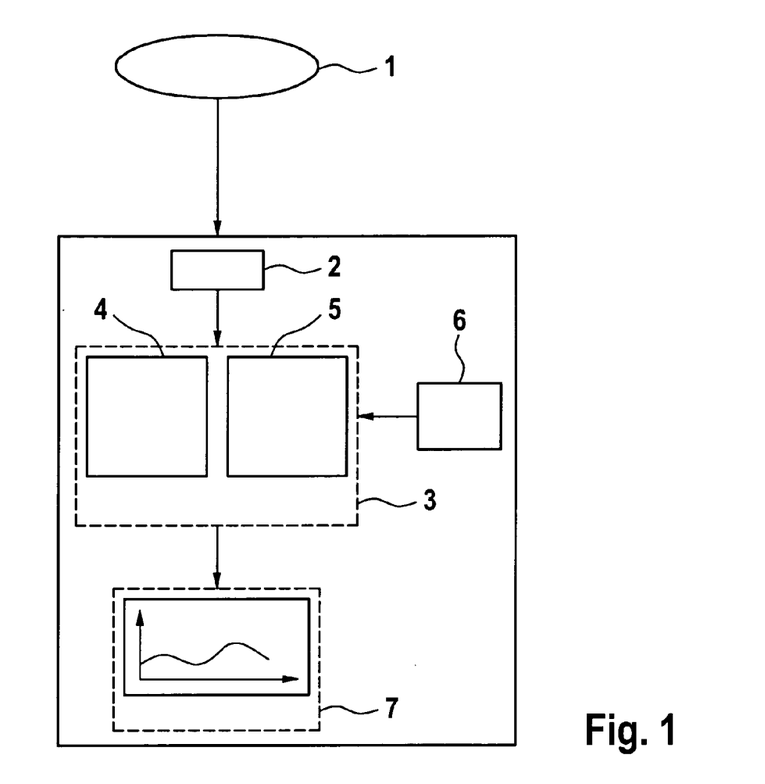
FIG. 1 shows a block diagram of a device according to the invention.

The essential components of a device according to the invention are shown in FIG. 1. A sensor 1 measures values at consecutive points in time $t_n$. The resulting measurement signal is then transmitted—wireless in the case shown—to a receiver 2 which in turn transmits the measurement signal to an analytical unit 3 containing a microprocessor 4 and a data storage unit 5. Alternatively, both data and commands can be transmitted to the analytical unit 3 by an input unit 6. The results are output by an output unit 7 which may include a display and other common output means. It is self-evident that data processing in the analytical unit 3 is performed in a digital fashion, and corresponding transformers for transforming analogous signals into digital signals are provided. More detailed explanations are not required in this context, since the basic design of devices of this type is known (from U.S. Pat. No. 5,507,288, for example) and the invention is suitable for a broad range of measuring techniques, in which—as described above—different measuring signals that are correlated with the desired working signal are measured.

Figure 2:
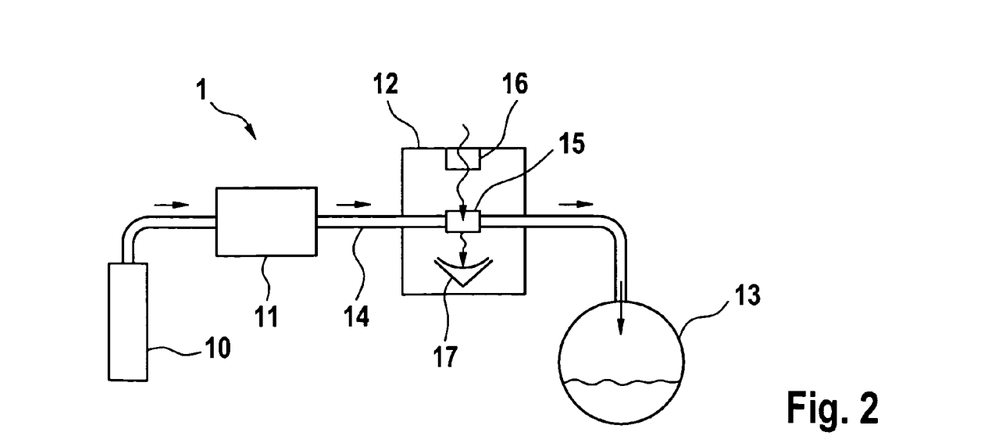
FIG. 2 shows a schematic sketch of a sensor suited for the invention.

FIG. 2 shows in the form of a schematic sketch a sensor 1, in which an implantable catheter 10 is used to aspirate interstitial fluid from the subcutaneous fatty tissue by means of a pump 11 and to aspirate the fluid through a photometric measuring unit 12 into a disposal container 13. Inside the photometric measuring unit 12, the tubing 14, through which the fluid is being transported, contains a transparent measuring cell 15, into which primary light emitted by a light sensor 16 is guided. The secondary light resulting from passage of the measuring cell 15 is then measured by means of a photo-detector 17 and the resulting signal processed by means of measuring electronics (not shown) to generate a raw signal, which—as is shown in FIG. 1 in an exemplary fashion—is transmitted to an analytical unit 3. The analytical unit 3 is used to determine from the raw signal analyte values $y(t_n)$ that are correlated with the concentration to be determined for consecutive points in time $t_n$. In the scope of the exemplary embodiment, these analyte values $y(t_n)$ represent the blood glucose level of a subject at a time $t_n$.

It is self-evident that the analyte values $y(t_n)$ can also be determined by other methods, for example methods based on an enzymatic conversion of glucose and subsequent electrochemical detection of the hydrogen peroxide formed in the process.

Figure 3:
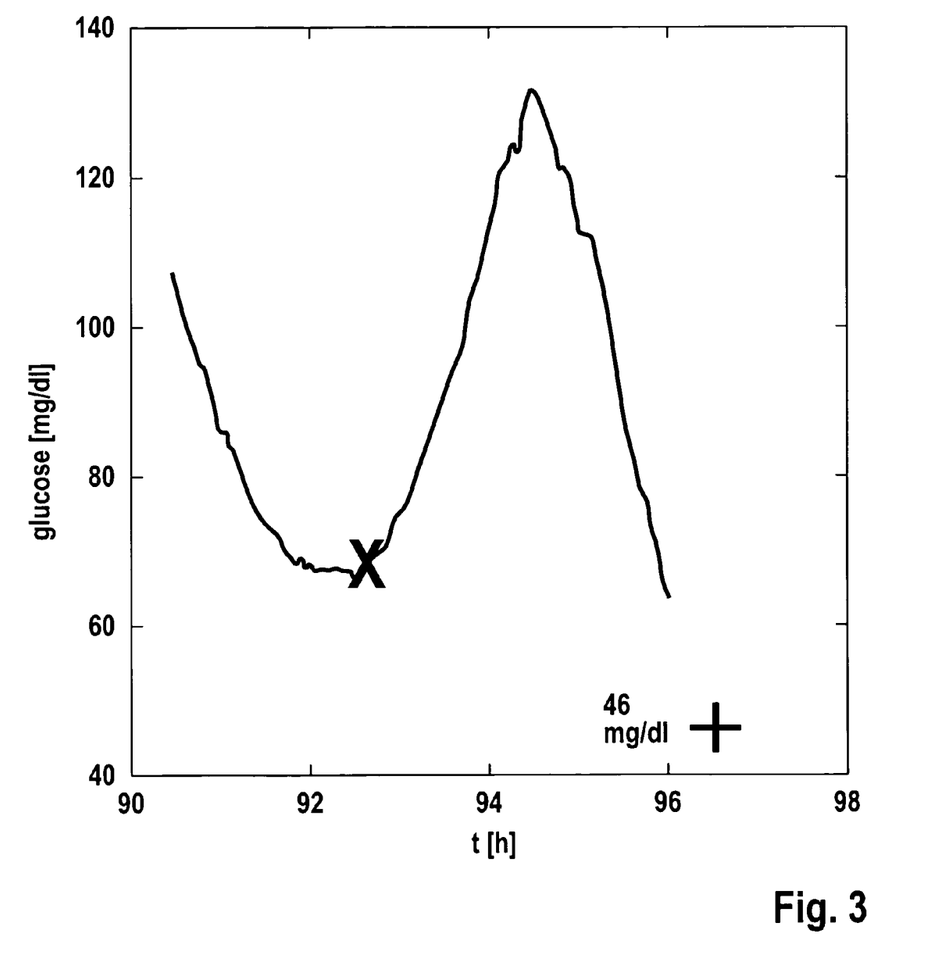
FIG. 3 shows a measuring signal of a sensor according to FIG. 2.

FIG. 3 shows a curve representing the progression of the blood glucose level of a subject. The two crosses drawn in FIG. 3 denote, in an exemplary fashion, one prediction value each that was determined for a prediction period of 30 minutes by the method to be described in the following. As shown by the good agreement of the left cross and the curve represented as a continuous line, the accuracy of the predicted values is good. It is self-evident that this applies only if the blood glucose level is not affected by an administration of insulin or uptake of carbohydrates during the prediction interval. The right cross in FIG. 3 shows a prediction value that is below a critical threshold value. In the case of a prediction value being this low, a warning signal is generated in order to alert a patient to a dangerous decrease in the blood glucose level such that the decrease can be counteracted by ingestion of carbohydrates.

The analyte values $y(t_n)$ shown in FIG. 3 in the form of a curve were determined from measured values that were recorded at intervals of 1 second each. To use a measuring rate this high is advantageous in that sufficient data is available for statistical processing of the measured values, but it is not obligatory. For many applications, it is sufficient to determine measured values at intervals of a few minutes e.g. every 2 to 5 minutes.

In the embodiment shown, the measured values were processed by means of a filter algorithm that includes an operation, in which the influence of a current measured value on the working signal is weighted by means of a weighting factor ("controllable filter algorithm"), whereby a signal variation parameter (related in each case to the current point in time, i.e. changing over time) is determined on the basis of signal variations detected in a close temporal relationship to the measurement of the current measured value, and the weighting factor is adapted dynamically as a function of the signal variation parameter determined for the current measured value for the point in time. Filter algorithms of this type are known as Kalmann filter algorithms and have been described, for example, in DE 10343863.7, the content of which is made a content of the present application by way of reference.

For the purposes of the method described in the following, extensive statistical processing of the measured values is not obligatory. Alternatively, it is also feasible, for example, to average over several measured values to obtain an analyte value ($t_n$) or to obtain exactly one analyte value $y(t_n)$ from each measured value.

The analyte values $y(t_n)$ determined by the analytical unit 12 are then used for predicting a prediction value for an analyte value $y(t_{n0}+\Delta t)$ over a prediction period $\Delta t$. The prediction values are predicted by first determining a function, $F(t_k, t_{k-\Delta n}, t_{k-2\Delta n}, \ldots, t_{k-(m-2)\Delta n}, t_{k-(m-1)\Delta n})$, the function F depends on analyte values $y(t_k)$, $y(t_{k-\Delta n})$, $y(t_{k-2\Delta n})$, $\ldots$, $y(t_{k-(m-2)\Delta n})$, $y(t_{k-(m-1)\Delta n})$. The function F which can be used to approximate the progression of the analyte values $y(t_n)$ at time $t_{n0}$ in a vicinity U of an analyte value $y(t_{n0})$ with a pre-determined accuracy $\sigma$, such that $$\sigma^2 \geq \sum_{t_k \in U} [y(t_k) - F(t_k - \Delta t, t_{k-\Delta n} - \Delta t, t_{k-2\Delta n} - \Delta t, \ldots, \quad \text{(eq. 1)}$$

$$t_{(k-(m-2)\Delta n)} - \Delta t, t_{(k-(m-1)\Delta n)} - \Delta t)]^2.$$

Whereby $\Delta n$ is an integer.

The function F is used by the analytical unit 12 to calculate a prediction value using the following equation:

$$y(t_{n0}+\Delta t)=F(t_{n0}, t_{n0-\Delta n}, \ldots, t_{(n0-(m-2)\Delta n)}, t_{(n0-(m-1)\Delta n)}) \quad \text{(eq. 2)}.$$

The concentration of an analyte that is present therein is mathematically treated as a deterministic dynamic system with some possible interference by noise. The development of this system over time is then described as a phase trajectory in a phase space whose dimensionality depends on the number of independent variables influencing the concentration of the analyte to be determined. In the case of diabetes, for example, the number of ingested bread units and the quantity of insulin administered are variables of this type, on which future values of the blood glucose concentration depend.

For practical purposes, the number of variables, on which the analyte concentration to be determined depends, is usually unknown and consequently the dimensionality of the phase space, in which the development of the system over time can be described by means of the phase trajectory, is also unknown.

The invention utilizes the fact that there is no need to know the entire phase trajectory of the system in a possibly high-dimensional phase space in order to be able to predict an analyte value. For extrapolating a point on the phase trajectory it is only necessary to know the phase trajectory in a vicinity of that point. In particular, there is no need to consider the entire phase space of the system for extrapolation, but rather it is sufficient to study the dynamics in an artificial, reconstructed phase space of significantly lower dimensionality.

It is sufficient if the dimensionality is high enough to account for all dominant degrees of freedom driving the dynamics of the system. Degrees of freedom with a negligible effect on the dynamics of the system can be left unaccounted for such that the dimensionality of the reconstructed phase space can be selected accordingly lower.

Negligible degrees of freedom are found especially for dynamic systems, in which a sub-system is weakly coupled to the remaining system. Considering diabetes as an example, a sub-system, that depends on the administered quantity of insulin, ingested bread units and physical exercise, is weakly coupled to hormonal regulation mechanisms, which also exert an influence on the blood sugar levels.

A time series of analyte values $y(t_n)$ determined for consecutive points in time $t_n$ contains in principle all of the information regarding the dynamic behavior of the system. Therefore, from a finite number of analyte values $y(t_n)$ determined for consecutive points in time $t_n$—often as few as approx. 10 analyte values in the vicinity of the point to be extrapolated are sufficient—a local approximation of the phase trajectory in the vicinity of an analyte value $y(t_{n0})$ at point in time $t_{n0}$ can be determined and extrapolated into the future by a prediction period $\Delta t$ such that a prediction value of an analyte value $y(t_{n0}+\Delta t)$ can be calculated.

It is important that the analyte values used to determine the function F and thus a local approximation of the phase trajectory were not determined for points in time $t_n$ that are too close to each other. Otherwise there is a risk that an observed progression is based mainly on measuring errors and noise effects and does not reflect the dynamics over time of a concentration change of the analyte.

In order to be able to reduce the influence of inevitable measuring errors to the extent possible by statistical methods it is desired to determine analyte values $y(t_n)$ for consecutive points in time $t_n$ that are as close to each other as possible. Therefore, it may be necessary not to use all analyte values $y(t_n)$ determined for directly consecutive points in time $t_n$ for determining a local approximation of the phase trajectory, but rather only every second, third or n-th such analyte value that has been determined.

For this reason, equation 1 includes a parameter $\Delta n$ to ensure that the analyte values $y(t_n)$ that are used to determine the function F were measured for consecutive points in time $t_n$ that are separated by sufficiently large time intervals.

Whether or not a function F as determined can be used to approximate the time profile of the analyte values $y(t_n)$ with a pre-determined accuracy, can be tested by means of equation 1. In principle, it is necessary to sum up over all points in time $t_k$ from the vicinity U of the analyte value $y(t_{n0})$ at time $t_{n0}$. However, this does not exclude that individual analyte values $y(t_n)$ recognized as erroneous, for example by means of applying suitable filters, are ignored. The function F can be a non-linear function and depend not only on the analyte values, but in addition on their first and second time derivative. The function F approximates the progression of the analyte values in a vicinity U of a point in time $t_{n0}$ at a pre-determined accuracy $\sigma^2$. Although the progression of the analyte values $y(t_n)$ is usually not linear, however, it is preferable for the function F to be a linear function. It has proven to be particularly favorable to represent the function F using coefficients $a_0$ to $a_m$ suffices as follows:

$$F = a_0 + \sum_{j=1}^{m} y(t_{k-(m-j)\Delta n})a_j$$

The value of the parameter, m, of function $F(t_k, t_{k-\Delta n}, t_{k-2\Delta n}, \ldots, t_{k-(m-2)\Delta n}, t_{k-(m-1)\Delta n})$ (e.g. in $a_m$ and $t_{k-(m-1)\Delta n}$) describes the dimensionality of the phase space, in which the dynamical behavior of the system is approximated.

The coefficients, $a_0$ to $a_m$, can be determined by minimizing the equation for various analyte values $y(t_k)$ from the vicinity U.

$$\sigma^2 \geq \sum_{t_k \in U} \left[ y(t_k) - a_0 - \sum_{i=1}^{m} y(t_{k-(m-i)\Delta n}) - \Delta t)a_i \right]^2$$

The vicinity U must be selected such that it contains a sufficient number of points in time $t_n$ for the determination of the coefficients, $a_0$ to $a_m$. If measured values are detected at a high measuring rate and analyte values $y(t_n)$ are determined for accordingly tightly spaced points in time $t_n$, it is advantageous not to include each and every analyte value that was determined in the equation above for the determination of the coefficients $a_0$ bis $a_m$, but instead, for example, only every second or third analyte value such that $\Delta n$ is not necessarily equal to 1, but rather can be a different integer. Although, in principle, the sum for all points in time $t_k$ in the vicinity U of the time $t_{n0}$ should be obtained in the equation stated above, this does not exclude that analyte values $y(t_k)$ recognized to be outliers, for example by means of suitable filters, are not included in the analysis.

Ideally, the times $t_n$, for which the analyte values $y(t_n)$ are determined, should be at equidistant time intervals from each other. However, analyte values in a living body of a human or animal possess such high auto-correlation when viewed over extended periods of time, that minor deviations from a constant measuring rate affect the accuracy of the prediction values only to a small degree. For example, the concentrations of lactate—under aerobic conditions—or creatinine display high auto-correlation over a period of several hours. Even relatively rapidly varying analytes, such as glucose, show an auto-correlation coefficient in excess of 0.8 over a period of 30 minutes.

The value of the parameter m in the function $F(t_k, t_{k-\Delta n}, t_{k-2\Delta n}, \ldots, t_{k-(m2)\Delta n}, t_{k-(m-1)\Delta n})$, i.e. the dimensionality of the relevant phase space, cannot be stated generally for all possible cases, in which the concentration of an analyte in the living body of a human or animal must be monitored. This is due mainly to the fact that the concentration of the various analytes of medical interest depend on different numbers of independent variables. In the case of the blood glucose concentration of a diabetes patient, two such variables are known, i.e. the quantity of bread units ingested and the quantity of insulin administered. In general, it can be said that the parameter does not need to be larger than twice the number of independent variables plus 1. Therefore, m=5 in the present exemplary embodiment illustrated by means of FIG. 3.

As has been mentioned above, the value of the parameter m corresponds to the dimensionality of a phase space reconstructed according to the "Takens time delay embedding" method, in which the dynamic behavior of the system can be described. For practical purposes, m usually has at most a value between 3 and 10, preferably between 5 and 8, and can be determined empirically. One option for determining the dimensionality of the phase space and thus the value of this parameter is provided by the method of so-called "false nearest neighbour" analysis as described in a publication by M. B. Kennel et al., Phys. Rev. A 45 3403 (1995). Reference is made to this publication in a supplementing fashion such that the content thereof is incorporated in the present application by way of reference.

Once the coefficients, $a_0$ to $a_m$, have been determined they can be used to calculate a prediction value $$y(t_{n0} + \Delta t) = a_0 + \sum_{j=1}^{m} y(t_{(n0-(m-j)\Delta n)})a_j$$

Subsequently, a prediction value determined accordingly is compared to a predetermined lower and/or upper threshold value and a warning signal is generated if that value is below or above the threshold value, respectively.

When a patient responds to a warning signal of this type by ingesting carbohydrates or administering a dose of insulin, it takes a while before the blood glucose concentration is affected by such ingestion of carbohydrates or administration of insulin. For this reason, it is usually necessary to predict analyte value 10 to 90 minutes, preferably 20 to 40 min, into the future such that there is sufficient time to counteract a dangerous increase or decrease of the analyte concentration. It has been found that analyte values are better predicted over extended periods of time if, rather than selecting an accordingly large prediction period (e.g. $\Delta t=30$ min) in a single step, the procedure is applied in multiple smaller steps of 5 minutes, for example. In each additional step coefficients $a_0$ to $a_m$ are determined for an already calculated prediction value $y(t_{n0}+\Delta t)$, which coefficients are used to approximate the progression of analyte values $y(t_n)$ in a vicinity U of the analyte value at point in time $t_{n0}+\Delta t$. The results are used to calculate another prediction value $y(t_{n0}+2\Delta t)$. In a stepwise procedure of this type, the prediction period $\Delta t$ of the individual steps should be selected to be equal to the interval between times $t_n$, for which the analyte values $y(t_n)$ used for calculating the prediction values were determined. If the time interval between consecutive points in time $t_n$ equals dt, this means that the prediction period is given by $\Delta t=dt \cdot \Delta n$. In the process, it is important that the coefficients, $a_0$ to $a_m$, used to approximate the progression of the analyte values in the vicinity U are re-determined in each step for a vicinity U that is shifted by the prediction period $\Delta t$.

Instead of predicting an analyte value $y(t_n)$ for a point in time $t_n$ in the future by means of multiple application of the method in multiple steps, it is also feasible to use a suitably larger prediction period $\Delta t$ and coefficients, $a_0$ to $a_m$, determined accordingly to predict in a single step an analyte value $y(t_n+\Delta t)$ in the distant future.

Figure 4:
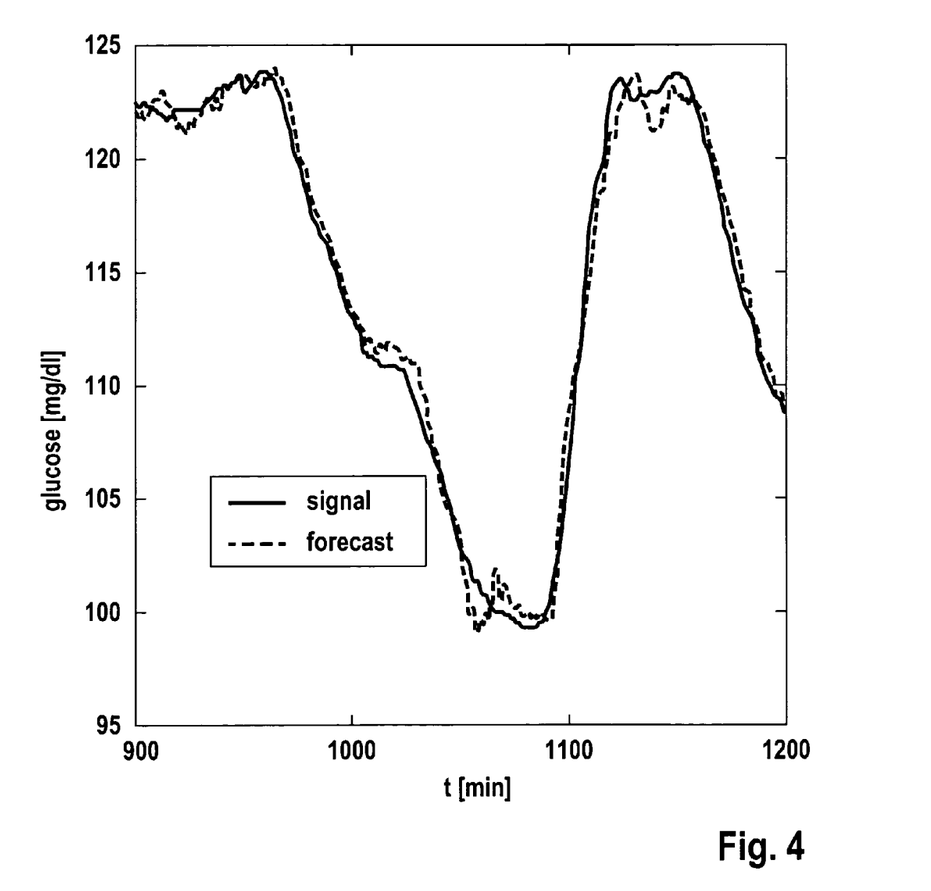
FIG. 4 shows measured blood glucose concentration values and blood glucose concentration values predicted for a period of 30 minutes.

The method described above cannot only be used to predict future analyte values, but also to test analyte values $y(t_n)$ that were determined for the past and identify false analyte values $y(t_n)$ which are due to outliers or measuring errors. The generally very good agreement between the measured analyte values $y(t_n)$ and the prediction values is shown in FIG. 4 in an exemplary fashion. The smooth continuous curve represents the time profile of the prediction values, whereas the curve showing strong short-term variations represents the time profile of the measured values. The prediction period was 2 min, and a total of 15 steps were performed consecutively such that analyte values were predicted for a period of 30 minutes. Therefore, the y axis does not represent the blood glucose concentration in FIG. 4, but rather the intensity of the measuring signal on which the blood glucose determination is based as detected electrochemically (in units of nanoampere).

The finding that the dynamic behavior of a deterministic system can be described by a finite number of analyte values $y(t_n)$ that are determined for consecutive points in time $t_n$, on which the function F depends, is based on the "Takens time delay embedding" method described in the publication by T. Schreiber in Phys. Rep. 85, 1–64 (1999). According to the terminology used in the publication of T. Schreiber, the interval between consecutive points in time, for which analyte values $y(t_n)$ are determined, is called delay time. Reference is made to the publication of T. Schreiber in a supplementing fashion such that the content thereof is incorporated in the present application by way of reference. For the calculation, it can be advantageous to transform the coordinates $y(t_k)$, $y(t_{k-\Delta n})$, $y(t_{k-2\Delta n})$, . . . , $y(t_{k-(m-2)\Delta n})$, $y(t_{k-(m-1)\Delta n})$ and determine F as a function of a set of transformed coordinates $Ty(t_k)$, $Ty(t_{k-\Delta n})$, . . . , $Ty(t_{k-(m-1)\Delta n})$.

Figure 5:
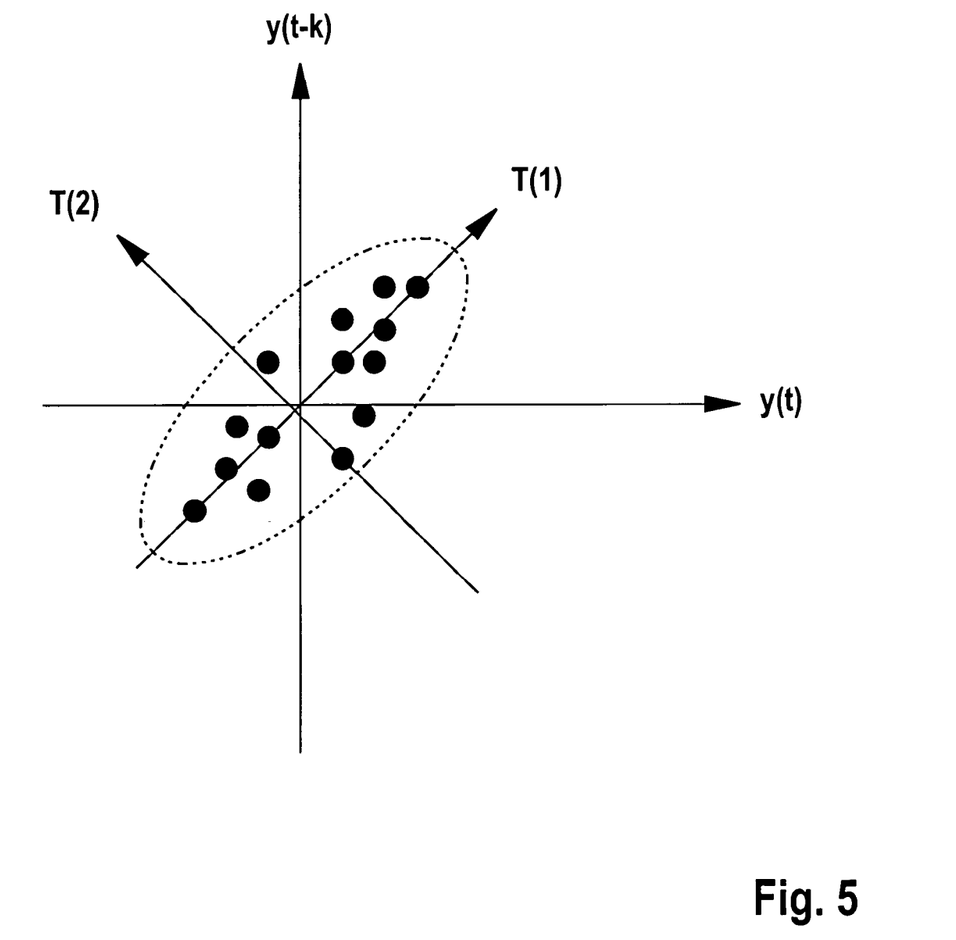
FIG. 5 shows a schematic example of a phase space with data points.

It is preferable to perform a linear transformation on the set of coordinates. Hereby, it is useful for the transformed coordinates to be so-called latent coordinates aligned along the main axes of a so-called ellipsoid of variance, as is illustrated in FIG. 5. An ellipsoid of variance of this type is drawn in a two-dimensional phase space in FIG. 5, which phase space is represented by its delay coordinates, y(t) and y(t-k). The ellipsoid of variance surrounds data points that are indicated by black circles, which, when connected according to their sequence in time, form a phase trajectory.

The ellipsoid of variance can be calculated from the scattering of the data points in the phase space, whereby the main axes of the ellipsoid indicate the variance of the data points in the corresponding direction of the phase space. FIG. 5 also shows the new phase space obtained by transformation along with its coordinates, T(1) and T(2). The first latent coordinate T(1) extends along the largest axis of inertia of the ellipsoid of variance, the second latent coordinate T(2) along the second-to-largest axis of inertia. Numerically, a transformation to latent coordinates can be performed for example by so-called principal component analysis (M. Otto, Chemometrics, Wiley, Weinheim (Germany), 1999, pages 124 to 133) or singular value decomposition (W. H. Press et al., Numerical Recipes, Cambridge University Press, Cambridge (UK), 1989, pages 52 to 61).

By performing a transformation to latent coordinates of this type, it is possible to achieve that one or several of the transformed coordinates have a negligible effect on the function F at the predetermined accuracy σ such that only a correspondingly smaller number of transformed coordinates needs to be included in the analysis in the calculation of function F.

These and other features and advantages of the present invention should be more fully understood from the above detailed description of the invention taken together with the accompanying claims. It is noted that the scope of the claims is defined by the recitations therein and not by the specific discussion of the features and advantages set forth in the present description.

It is noted that terms like "preferably", "commonly" and "typically" are not utilized therein to limit the scope of the claimed invention or to imply that certain features are critical, essential or even important to applications of the claimed invention. Rather, these terms are merely intended to highlight alternative or additional features that may or may not be utilized in a particular embodiment of the present invention.

It is noted that terms like "preferably", "commonly", and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

For the purposes of describing and defining the present invention it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may very from a stated reference without resulting in a change in the basic function of the subject matter at issue.

Having described the invention in detail and by reference to specific embodiments thereof, it will be apparent that modification and variations are possible without departing from the scope of the invention defined in the appended claims. More specifically, although some aspects of the present invention are identified herein as preferred or particularly advantageous, it is contemplated that the present invention is not necessarily limed to these preferred aspects of the invention.

What is claimed is:

1. A method for continuous monitoring of an analyte concentration in the living body of a human or animal, the method comprising:
   determining an analyte values $y(t_n)$ correlating with the concentration of the analyte for consecutive points in time $t_n$;
   calculating a prediction value $y(t_{n0}+\Delta t)$ over a prediction period $\Delta t$ based on the analyte value $y(t_n)$ using the following equation:

$$y(t_{n0}+\Delta t) = F(t_{n0}, t_{n0-\Delta n}, \ldots, t_{n0-(m-2)\Delta n}, t_{n0-(m-1)\Delta n}); \text{ and}$$

generating a warning signal if the prediction value $y(t_{n0}+\Delta t)$ deviates from a predetermined value by more than a threshold value,
   wherein function $F(t_k, t_{k-\Delta n}, t_{k-2\Delta n}, \ldots, t_{k-(m-2)\Delta n}, t_{k-(m-1)\Delta n})$ depends on the analyte values $y(t_k)$, $y(t_{k-\Delta n})$, $y(t_{k-2\Delta n})$, ..., $y(t_{k-(m-2)\Delta n})$, $y(t_{k-(m-1)\Delta n})$ and the function F is used to approximate the progression of the analyte values $y(t_n)$ at time $t_{n0}$ in vicinity U of an analyte value $y(t_{n0})$ with a pre-determined accuracy $\sigma$, such that $$\sigma^2 \geq \sum_{t_k \in U} [y(t_k) - F(t_k - \Delta t, t_{k-\Delta n} - \Delta t, t_{k-2\Delta n} - \Delta t, \ldots t_{k-(m-2)\Delta n} - \Delta t, t_{k-(m-1)\Delta n} - \Delta t)]^2$$

whereby $n_0$, m, and $\Delta n$ are integers.

2. The method according to claim 1, wherein the function F depends not only on analyte values $y(t_k)$, $y(t_{k-\Delta n})$, $y(t_{k-2\Delta n})$, ..., $y(t_{k-(m-2)\Delta n})$, $y(t_{k-(m-1)\Delta n})$, but in addition on their first time derivatives.

3. The method according to claim 1, wherein the function F depends not only on analyte values $y(t_k)$, $y(t_{k-\Delta n})$, $y(t_{k-2\Delta n})$, ..., $y(t_{k-(m-2)\Delta n})$, $y(t_{k-(m-1)\Delta n})$, but in addition on their first and second time derivatives.

4. The method according to claim 1, wherein the function F contains linear or square terms.

5. The method according to claim 1, wherein the function F is a linear function.

6. The method according to claim 1, wherein the function F can be represented by coefficients $a_0$ to $a_m$ as follows:

$$F = a_0 + \sum_{j=1}^{m} y(t_{(k-(m-j)\Delta n)}) a_j.$$

7. The method according to claim 6, wherein the coefficients, $a_0$ to $a_m$, are determined by minimizing the sum $$\sum_{t_k \in U} \left[ y(t_k) - a_0 - \sum_{i=1}^{m} y(t_{(k-(m-i)\Delta n)} - \Delta t) a_i \right].$$

8. The method according to claim 6, wherein the coefficients, $a_0$ to $a_m$, are determined by solving a system of linear equations which contains one equation each of the type $$y(t_k) = a_0 + \sum_{j=1}^{m} y(t_{(k-(m-j)\Delta n)} - \Delta t) a_j$$

for at least m+1 different analyte values $y(t_k)$ from the vicinity U of the point in time $t_{n0}$.

9. The method according to claim 8, wherein the system of equations contains more than m+1 equations and is solved numerically by approximation to determine the coefficients, $a_0$ to $a_m$.

10. The method according to claim 1, wherein the analyte values $y(t_n)$ used to determine the function F are obtained by numerical processing, in particular by filtering, of measured values.

11. The method according to claim 1, wherein the analyte values $y(t_n)$ used to calculate the prediction value are determined from consecutive points in time $t_n$ which are separated by intervals of 30 seconds to 5 minutes, preferably by 1 to 3 minutes.

12. The method according to claim 1, wherein the analyte values $y(t_n)$ used to calculate the prediction value or one of the prediction values are determined for times $t_n$ which are separated by an interval corresponding to the prediction period $\Delta t$.

13. The method according to claim 1, wherein the number of the coefficients, $a_0$ to $a_m$, is 4 to 11, preferably 6 to 9.

14. The method according to claim 1, wherein the function F is determined as a function of transformed coordinate values $Ty(t_k)$, $Ty(t_{k-\Delta n})$, $Ty(t_{k-2\Delta n})$, ..., $Ty(t_{k-(m-2)\Delta n})$, $Ty(t_{k-(m-1)\Delta n})$, which were determined by means of a transformation, preferably a linear transformation, from analyte values $y(t_k)$, $y(t_{k-\Delta n})$, $y(t_{k-2\Delta n})$, ..., $y(t_{k-(m-2)\Delta n})$, $y(t_{k-(m-1)\Delta n})$, whereby the transformation is selected such that at least one of the values $Ty(t_k)$, $Ty(t_{k-\Delta n})$, $Ty(t_{k-2\Delta n})$, ..., $Ty(t_{k-(m-2)\Delta n})$, $Ty(t_{k-(m-1)\Delta n})$ has a negligible influence on the function F at the predetermined accuracy $\sigma$.

15. A method for continuous monitoring of an analyte concentration in the living body of a human or animal, the method comprising:
   determining an analyte values $y(t_n)$ correlating with the concentration of the analyte for consecutive points in time $t_n$;

calculating a prediction value $y(t_{n0}+\Delta t)$ over a prediction period $\Delta t$ based on the analyte value $y(t_n)$ using the following equation:

$$y(t_{n0}+\Delta t)=F(t_{n0},\ t_{n0-\Delta n},\ \ldots,\ t_{n0-(m-2)\Delta n},\ t_{n0-(m-1)\Delta n})$$

generating a warning signal if the prediction value $y(t_{n0}+\Delta t)$ deviates from a predetermined value by more than a threshold value, wherein function $F(t_k,\ t_{k-\Delta n},\ t_{k-2\Delta n},\ \ldots\ t_{k-(m-2)\Delta n},\ t_{k-(m-1)\Delta n})$ depends on the analyte values $y(t_k)$, $y(t_{k-\Delta n})$, $y(t_{k-2\Delta n})$, ..., $y(t_{k-(m-2)\Delta n})$, $y(t_{k-(m-1)\Delta n})$; and adapting the function $F(t_k,\ t_{k-\Delta n},\ t_{k-2\Delta n},\ \ldots,\ t_{k-(m-2)\Delta n},\ t_{k-(m-1)\Delta n})$ in a vicinity U of an analyte value $y(t_{n0}+\Delta t)$ at a point in time $t_n=t_{n0}+\Delta t$ for a calculated prediction value $y(t_{n0}+\Delta t)$, such that the adapted function F approximates the progression of analyte values $y(t_n)$ in the vicinity U with a predetermined accuracy and an additional prediction value $y(t_{n0}+2\Delta t)$ is calculated therefrom, whereby $n_0$, $m$, and $\Delta n$ are integers.

* * * * *

UNITED STATES PATENT AND TRADEMARK OFFICE
CERTIFICATE OF CORRECTION

PATENT NO. : 7,188,034 B2
APPLICATION NO. : 11/113606
DATED : March 6, 2007
INVENTOR(S) : Staib et al.

It is certified that error appears in the above-identified patent and that said Letters Patent is hereby corrected as shown below:

On Title Page
In the Abstract Item 57:

line 5, "the concentration to be determined are determined for consecutive" should be changed to --the concentration to be determined for consecutive--.

line 7, "predict a prediction value for" should be changed to --predict prediction value for--.

In the specification:

Column 1, line 17, "analyte value" should be changed to --analyte values--.

Column 2, line 13, "A method for continuous" should be changed to --A method is proposed for continuous--.

Column 2, line 22, "$y(t_0+2\Delta t)$" should be changed to --$y(t_{n0}+2\Delta t)$--.

Column 2, line 23, "$y(t_0+n\Delta t)$" should be changed to --$y(t_{n0}+n\Delta t)$--.

Column 2, line 29, "is definitely by" should be changed to --is defined by--.

Column 4, line 15, "value $(t_n)$ or to" should be changed to --value $y(t_n)$ or to--.

Column 4, line 24, "which can be used" should be changed to --can be used--.

Column 4, line 33, "Whereby" should be changed to --whereby--.

Column 9, line 36, "and" should be the first word on Column 9, line 37 --and generating--.

Column 10, line 65, "determining an analyte" should be changed to --determining analyte--.

UNITED STATES PATENT AND TRADEMARK OFFICE
CERTIFICATE OF CORRECTION

PATENT NO. : 7,188,034 B2
APPLICATION NO. : 11/113606
DATED : March 6, 2007
INVENTOR(S) : Staib et al.

It is certified that error appears in the above-identified patent and that said Letters Patent is hereby corrected as shown below:

Column 11, line 2, "value" should be changed to --values--.

Signed and Sealed this

Fourth Day of September, 2007

JON W. DUDAS
*Director of the United States Patent and Trademark Office*